US009964525B2

(12) United States Patent  
Auffray et al.

(10) Patent No.: US 9,964,525 B2  
(45) Date of Patent: May 8, 2018

(54) AUTOMATIC CALIBRATION METHOD FOR CHECKING BY ULTRASOUND A COMPOSITE MATERIAL STRUCTURE DURING PRODUCTION

(71) Applicant: AIRBUS SAS, Blagnac (FR)

(72) Inventors: Stéphane Auffray, Saint Lyphard (FR); Hubert Voillaume, Issy les Moulineaux (FR)

(73) Assignee: Airbus SAS, Blagnac (FR)

( * ) Notice: Subject to any disclaimer, the term of this patent is extended or adjusted under 35 U.S.C. 154(b) by 236 days.

(21) Appl. No.: 14/654,528

(22) PCT Filed: Dec. 17, 2013

(86) PCT No.: PCT/EP2013/076901  
§ 371 (c)(1),  
(2) Date: Sep. 23, 2015

(87) PCT Pub. No.: WO2014/095863  
PCT Pub. Date: Jun. 26, 2014

(65) Prior Publication Data  
US 2016/0041130 A1 Feb. 11, 2016

(30) Foreign Application Priority Data  
Dec. 21, 2012 (FR) ...................... 12 62545

(51) Int. Cl.  
*G01N 29/30* (2006.01)  
*G01N 29/11* (2006.01)  
*G01N 29/44* (2006.01)

(52) U.S. Cl.  
CPC ............. *G01N 29/30* (2013.01); *G01N 29/11* (2013.01); *G01N 29/4436* (2013.01); *G01N 2291/0231* (2013.01); *G01N 2291/106* (2013.01)

(58) Field of Classification Search  
CPC .............................................. G01N 2291/0251  
See application file for complete search history.

(56) References Cited

U.S. PATENT DOCUMENTS 3,888,114 A * 6/1975 Adams, Jr. ............... G01H 1/04  
                                                                                                  73/628  
5,095,754 A * 3/1992 Hsu ........................ B64D 15/20  
                                                                                                  340/962

(Continued)

FOREIGN PATENT DOCUMENTS

FR      2 930 344 A1    10/2009  
FR      2 995 556 A1     3/2014

*Primary Examiner* — Leslie J Evanisko  
*Assistant Examiner* — Ruben Parco, Jr.  
(74) *Attorney, Agent, or Firm* — Greer, Burns & Crain Ltd.

(57) ABSTRACT

A monitoring system comprising ultrasound sensors to monitor the structure of a composite material part during production is automatically calibrated using reference sensors mounted on reference blocks and placed in the production environment of the part. The automatic calibration comprises actuating a reference sensor to transmit an ultrasonic wave and measuring the amplitude of a reference echo constituted by the transmitted ultrasonic wave after it has passed through the reference block. The measured amplitude is compared to a set point value and the gain is applied to the reference sensor to obtain an amplitude value of the reference echo substantially equal to the set point value. The gain applied to the reference sensor is applied to the ultrasound sensors of the same type as the reference sensor. The operation is performed for each reference sensor, and successively for all of the stages of production of the part.

9 Claims, 4 Drawing Sheets

(56) References Cited

U.S. PATENT DOCUMENTS

| | | |
|---|---|---|
| 5,163,027 A | 11/1992 | Miller et al. |
| 2007/0101815 A1 | 5/2007 | Kollgaard et al. |
| 2009/0314088 A1* | 12/2009 | Djordjevic .......... G01N 29/028 73/602 |
| 2013/0047697 A1* | 2/2013 | Zhang ................. G01N 29/043 73/1.82 |
| 2015/0217485 A1 | 8/2015 | Aufray |

* cited by examiner

AUTOMATIC CALIBRATION METHOD FOR CHECKING BY ULTRASOUND A COMPOSITE MATERIAL STRUCTURE DURING PRODUCTION

RELATED APPLICATIONS

This application is a § 371 application from PCT/EP2013/076901 filed Dec. 17, 2013, which claims priority from French Patent Application No. 12 62545 filed Dec. 21, 2012, each of which is herein incorporated by reference in its entirety.

FIELD OF THE INVENTION

The invention relates to the general field of the production of parts made of composite materials and more specifically of parts made of fiber-reinforced resin matrix composite materials. It relates more particularly to the monitoring of such structures during the production process.

BACKGROUND OF THE INVENTION

The process of producing composite material parts generally comprises various temporally successive stages, with each stage having to be carried out at a given pressure and temperature which may be different from one step to the next.

Consequently, in order to effectively monitor the quality of the performance of a given stage, i.e. the quality of the product at each of the stages leading to the finished material, it is necessary to take these temperature and pressure parameters into account. This is particularly true when the monitoring is done by ultrasound insofar as the ambient temperature and pressure affect the response (sensitivity) of the ultrasonic sensors used.

It is noted that the use of ultrasonic sensors advantageously makes it possible to perform various monitoring functions such as:
 Characterizing the fiber preform formed by the flow of a resin injected into a fiber reinforcement (resin matrix/fiber reinforcement);
 Determining the advancement of the polymerization of the resin during the polymerization cycle itself;
 Determining the fiber volume ratio and/or the local porosity ratio.

In particular, ultrasound techniques are the only in-depth analysis techniques that make it possible to effectively monitor the absence of porosity in the material produced.

However, ultrasound monitoring is rarely used, at least in so-called "in-situ" fashion, insofar as measurements obtained by means of ultrasonic sensors are difficult to use precisely because of the variability of their sensitivity as a function of temperature and pressure, the levels of which are typically variable in the context of the production of composite material parts.

This is why alternate methods, for example based on dielectrometry (measurements of insulation resistance) or optical diffusion techniques, or systems using fiber optic Bragg gratings are generally used. However, such methods enable only local, non-volumetric measurements at the point where they are positioned, on the surface of or inside the part.

Moreover, even when ultrasonic sensors are used, their use is generally limited to measurements of ultrasound wave propagation times in the medium analyzed (i.e. the part being produced), with no consideration for, in particular, amplitude analysis.

SUMMARY OF THE INVENTION

An object of the invention is to propose a solution that makes it possible to use ultrasonic sensors to monitor composite material parts during the various stages of their production, which solution makes it possible to use ultrasonic sensors to perform both propagation time measurements and amplitude measurements, despite the temperature and pressure variations that may be imposed on the sensors.

To this end, a subject of the invention is a device for automatically calibrating an array of ultrasonic sensors for monitoring the structure of a composite material part during its production, the automatic calibration being performed during the production process. The device comprises an array of ultrasonic reference sensors. Each reference sensor is mounted on a calibration block and can be actuated so as to perform an amplitude measurement of a reference echo constituted by an ultrasonic wave transmitted by the sensor and having passed through the block on which the reference sensor is mounted. This array comprises at least one reference sensor for each of the types of measurement sensors used to monitor the structure of said part, each of the reference sensors being placed in proximity to the part in the same environment as the latter.

Depending on various dispositions or properties, possibly used in conjunction, the device according to the invention can also have the following additional features.

According to one embodiment, the device also comprises means for actuating each of the reference sensors at determined moments, performing the measurement of the amplitude of the reference echo received by this sensor, and determining the value of the gain control to be applied to this sensor in order to maintain the amplitude of the reference echo at a determined set point value.

According to another embodiment, the device also comprises means for applying to each of the measurement sensors a gain control whose value is a function of the value of the gain control determined for the reference sensor of the same type as the measurement sensor in question.

According to another embodiment, the device also comprises means for applying to each of the measurement sensors a gain control whose value is substantially equal to the value of the gain control determined for the reference sensor of the same type as the measurement sensor in question.

According to another embodiment, the blocks are made of a composite material identical to that forming the monitored part.

According to another alternative to the above embodiment, the blocks are made of silicon carbide or steel.

According to another embodiment, each ultrasonic reference sensor is mounted on a separate block.

Another object of the invention is a method for the automatic calibration of an array of ultrasonic sensors for monitoring the structure of a composite material part during its production. This method uses the device according to the invention to implement the following steps:
 a first step during which an excitation signal is applied to a reference sensor so as to cause it to transmit an ultrasonic wave through the reference block on which it is mounted, and the amplitude of the reference echo received by this sensor is measured;

a second step during which the value of the gain control to be applied to this sensor in order to obtain a reference signal with an amplitude value substantially equal to a set point value is determined;

a third step during which the gain control determined in the previous step is assigned to the measurement sensors of the same type as the reference sensor in question;

This three-step sequence being performed, for each of the reference sensors, at least once for each cycle (temperature, pressure) of the process for producing the composite material part.

The method according to the invention thus advantageously makes it possible to eliminate the influence of temperature on the response (sensitivity) of the ultrasonic sensors used to perform the monitoring.

It can be applied to any ultrasound monitoring means used in an environment whose variability over time (in temperature, hygrometry, salinity, pressure, etc.) can affect the sensitivity of the sensors.

DESCRIPTION OF THE FIGURES

The features and advantages of the invention will be better understood thanks to the following description, which description is based on the attached figures, which show.

DETAILED DESCRIPTION

Figure 1:
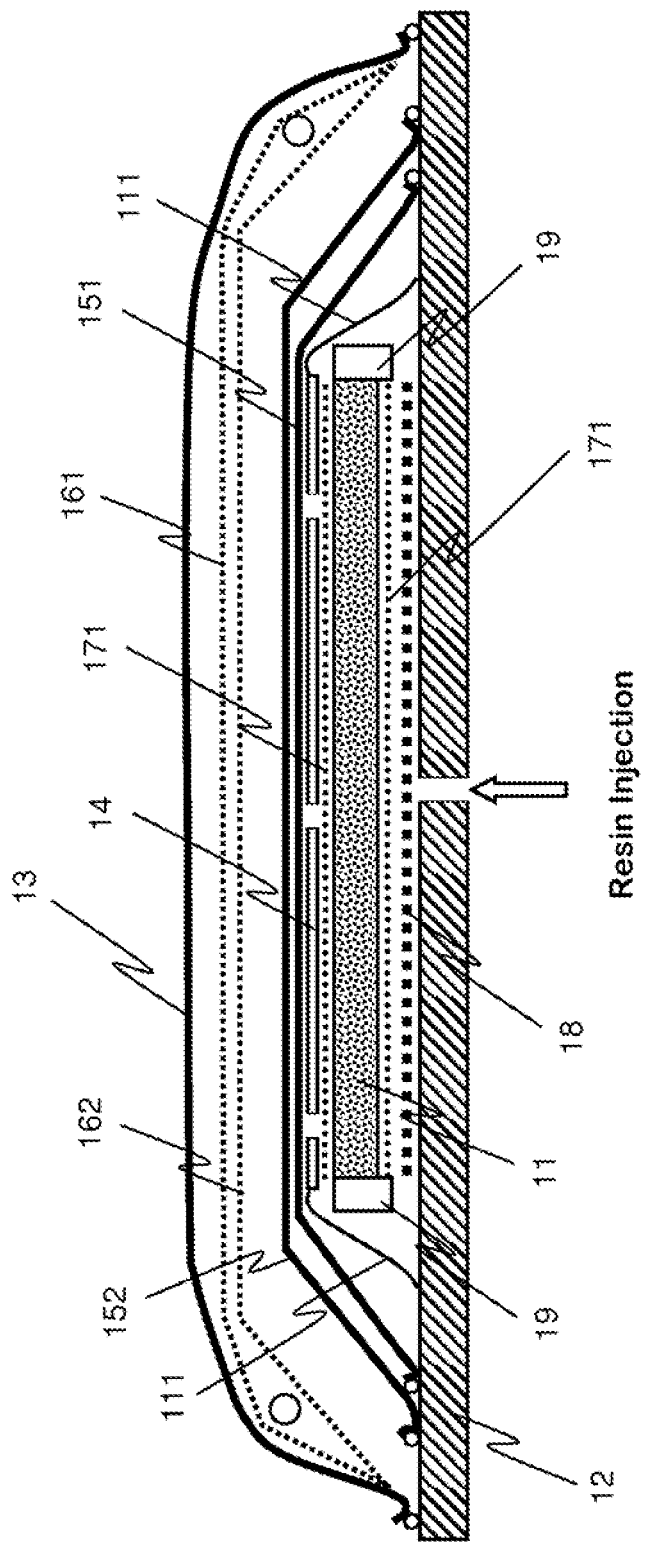
FIG. 1, the illustration related to the production of a composite material part according to the so called "LRI" method ("LRI" being the acronym for the term "Liquid Resin Infusion)

Hereinafter, the method according to the invention is described in terms of its application to the monitoring of a composite material structure according to the LRI method. This exemplary embodiment is presented as a nonlimiting example for the sole purpose of simply and clearly illustrating the features and advantages of the method according to the invention.

The LRI method makes it possible to produce composite material parts at low vacuum pressure. According to this method, a dry textile preform 11 is deposited in a mold 12 in an environment composed of draining 18 and release 171, 172 fabrics and one or more membranes 151, 152. The calibration of the thickness and the flatness of the part to be produced is enabled by a perforated metal plate 14 covering the preform, also known as a "caul-plate."

The injection method itself consists, in a known way, of injecting a resin into the mold, as illustrated by FIG. 1, in order to impregnate the preform 11, then of heating the resin and preform so as to obtain the polymerization of the resin. The heating temperature and the pressure inside the mold vary during production according to a given cycle, determined so as to obtain a part having the desired structural characteristics.

During the production phase, the state of the resin injected into the fibrous preform 11 thus changes under the combined effect of the temperature and the pressure, until a polymerization state is reached. The composite material part 11 thus formed then has a rigid structure.

During the production phase of the part 11 (i.e. the polymerization of the resin) it is generally advantageous to know the degree of advancement of the polymerization in order to ensure control over the process. Likewise, it is advantageous to be able to verify, during the production process itself, the health of the part, i.e., the structural integrity of this part, specifically verifying the absence of bubbles capable of giving the part an undesirable porosity, and the absence of a loss of cohesion between the folds forming the core of the part, which loss of cohesion results in a delamination of the part.

This is why measurement sensors, particularly ultrasonic sensors, are generally placed in proximity to the part 11 being produced, in order to perform an ultrasound scan of the internal structure of the part at the various stages of production, i.e. for the various cycles (temperature, pressure) to which the part 11 is subjected.

Figure 2:
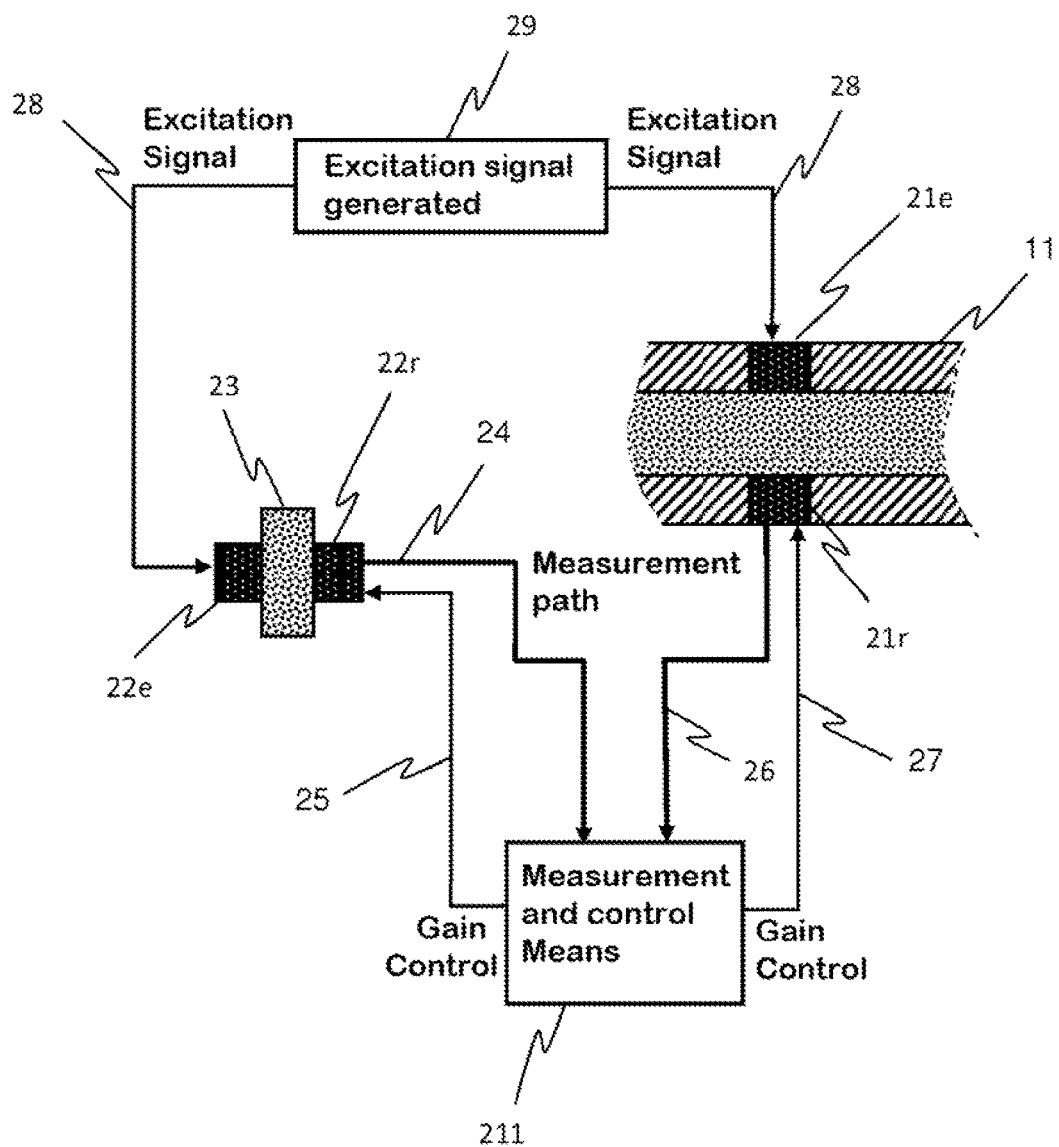
FIG. 2, a schematic illustration that makes it possible to describe the principle of the invention.

In a known way, depending on whether the standard of analysis in question is transmission or reflection analysis, the measurement sensors 21 are arranged either in proximity to each of the faces of the part to be produced, as illustrated by FIG. 2, one face being equipped with ultrasound transmitting devices 21e and the other face being equipped with receiving devices 21r; or, alternatively, on a single face, the devices used then being both transmitters and receivers.

Thus, in the configuration illustrated by FIG. 2, the ultrasound analysis can for example be performed using ultrasonic sensors 21, each comprising a transmitter 21e integrated into the "caul-plate" 14, these devices being distributed in a determined fashion on the surface of the latter and arranged so that their transmitting faces face the preform 11, and a receiver 21r integrated into the mold 12 and positioned facing the transmitting device of the same sensor, its receiving face being positioned facing the preform 11. French patent number FR1258703 filed by the applicant describes this arrangement in detail.

Such an arrangement of sensors makes it possible to perform an ultrasound monitoring of the changes in the state of the part 11 being produced (cross-linking, for example), particularly by measuring the propagation times of the sound waves transmitted through the material, but also by measuring the weakening of the ultrasonic waves passing through the material, which measurement makes it possible to determine its internal structure.

However, this measurement of the weakening is made difficult by the fact that the sensitivity of the ultrasound sensors 21 is variable as a function of temperature and pressure. In principle, the medium in which these sensors are placed, otherwise known as the chamber in which the production (i.e. the molding) of the part in question is carried out, is subject to temperature and pressure variations during the various stages of production.

Consequently, as the sensitivity of the sensors varies during the various stages, the measurements of the attenuation of the ultrasonic waves in the material being produced, obtained for the various production cycles using sensors disposed facing the preform 11, are generally difficult to use.

In order to solve this problem, the invention proposes the use of an automatic calibration that makes it possible, at any moment, to correct the variations in the sensitivity of the ultrasound sensors so as to obtain attenuation measurements independent of the temperature and pressure variations. The device for performing this automatic calibration is illustrated by the schematic representation of FIG. 2.

As FIG. 2 illustrates, the method according to the invention proposes to use a device comprising one or more reference sensors, according to which the ultrasound sensors used to monitor the part during production are either sensors of a same type or sensors of different types. In this second case, the device according to the invention comprises a reference sensor for each type of sensor used.

According to the invention, each reference sensor 22 is mounted on a test structure or reference block 23, the assembly being placed in the same environment as the part 11 being produced.

This reference block 23 is preferably made of a material having a structure such that the attenuation of the sound waves passing through this block is invariant in the range of temperatures and pressures in question, or at least such that the variation of the attenuation of the waves as a function of temperature and pressure is known. To this end, it is possible, for example to use a block made of silicon carbide or steel, whose mechanical properties, particularly the Young's modulus, vary little in the temperature range in question, typically from 20° C. to 200° C. (Young's modulus variations of less than 10%).

Moreover, the dimensions of this block are defined as a function of the width of the ultrasonic sensor so as to induce, in particular, a sufficient propagation time to clearly separate the echoes in the case of multiple reflections. Preferably, the dimensions of the blocks chosen are typically a length of 50 mm, a width of 50 mm, and a thickness of 5 mm. The sensors being disposed on 50 mm×50 mm faces, the thickness traversed by the ultrasonic wave is thus equal to 5 mm.

It should be noted that, knowing these attenuation properties, the amplitude of the ultrasonic wave being considered to be constant, it is possible to determine the variations in the reception gain of the ultrasonic reference sensor 22 mounted on the reference block 23 in question, this variation being, in particular, a function of the temperature and pressure variations to which this sensor is exposed. This variation can then be compensated by accordingly modifying the value of the gain control 25 applied to the receiver 221 of the reference sensor 22, so as to obtain as output 26 from this sensor a signal having a given constant level.

The modified value g' of the gain control 25 thus determined can then advantageously be used to modify, during the measurement phase, the gain of the receivers 212 of the measurement sensors 21 of the same type as the reference sensor 22 in question so as to compensate for the variations in the reception gain of these measurement sensors. In fact, these sensors 21 being of the same type as the reference sensor 22 and being placed in a same environment, the variation in the gain of these sensors is substantially identical to that of the gain of the reference sensor 22, so this variation can advantageously be corrected by applying to the receivers of the measurement sensors 21 a gain control 27 with a value equal to g'.

Figure 3:
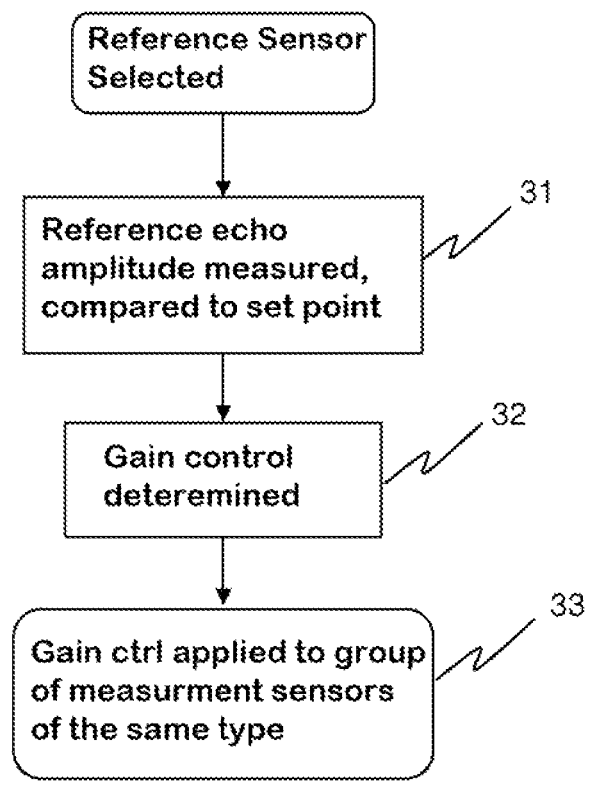
FIG. 3, a flow chart of the automatic calibration method according to the invention.

Consequently, the automatic calibration method according to the invention uses the determination of this gain variation to perform the calibration of the measurement sensors 21 that perform, during production, the monitoring of the composite material part in question. To this end, as FIG. 3 illustrates, the calibration method according to the invention implements the following steps:

a first step 31 during which, firstly, the electric excitation signal 28 delivered by a signal generator 29 is applied to the transmitter 22e of the reference sensor 22 in question so that it transmits an ultrasound signal of a given amplitude through the block 23 on which it is mounted, and during which, secondly, the amplitude of the measurement signal 24 corresponding to the ultrasonic reference echo received by the receiver 22r of the reference sensor 22 is measured, this echo corresponding to the transmitted ultrasonic wave after it has passed through the block 23.

a second step 32 during which the value g' of the gain control 25 to be applied to the receiver 22r of said reference sensor 22 is determined such that the amplitude of the measurement signal 24 has a value substantially equal to a determined set point value. This step is implemented, for example, by measurement and control means 211 which measure the amplitude of the signal transmitted 24, 26 by each sensor (measurement sensor or reference sensor) and separately control the gain control 25, 27, applied to each sensor.

The determination of this value is for example performed iteratively. With each iteration, a gain control 25 of a given value is applied to the reference sensor 22 and the level of the measurement signal supplied by the receiver 22r of this sensor is determined, this operation being reiterated until the value g' of the gain control 25 makes it possible to obtain a measurement signal 24 whose value is equal to the set point value.

This set point value is generally set so that the measurement signal 24 corresponding to the reference echo has a level markedly higher than the noise level without causing the sensor to become saturated.

a third step 33 during which the value of the gain control 27 to be applied to the receivers 21r of the measurement sensors 21 is modified so as to be made equal to the value of the gain control 25 determined during the second step.

According to the invention, this series of three steps is performed for the reference sensor in question, preferably at least once for each stage of production of the part 11 involving a change in the value of the temperature and/or the pressure. Thus, for each step, the gain control 27 of the various measurement sensors 21 can be adjusted so as to optimize the level of the echo detected by each sensor.

It should be noted that depending on the structure of the test system, the means used to drive the various sensors (measurement sensors or reference sensors) and to perform the testing operations and calibration operations may vary. Thus, it is possible to use means capable of driving all of the sensors simultaneously or means capable of driving the various sensors one after another. The exemplary embodiment illustrated by FIG. 4 corresponds to a measurement system configured to perform the monitoring of the various sensors sequentially rather than simultaneously.

In this exemplary application, which does not limit the subject or the scope of the invention presented here, the device for measuring the part 11 comprises two types of measurement sensors 21 and 41, so the calibration device according to the invention itself comprises two calibration sensors 22 and 42. The means for implementing the elements of the calibration device according to the invention in this case are also completely integrated into the measurement system.

Figure 4:
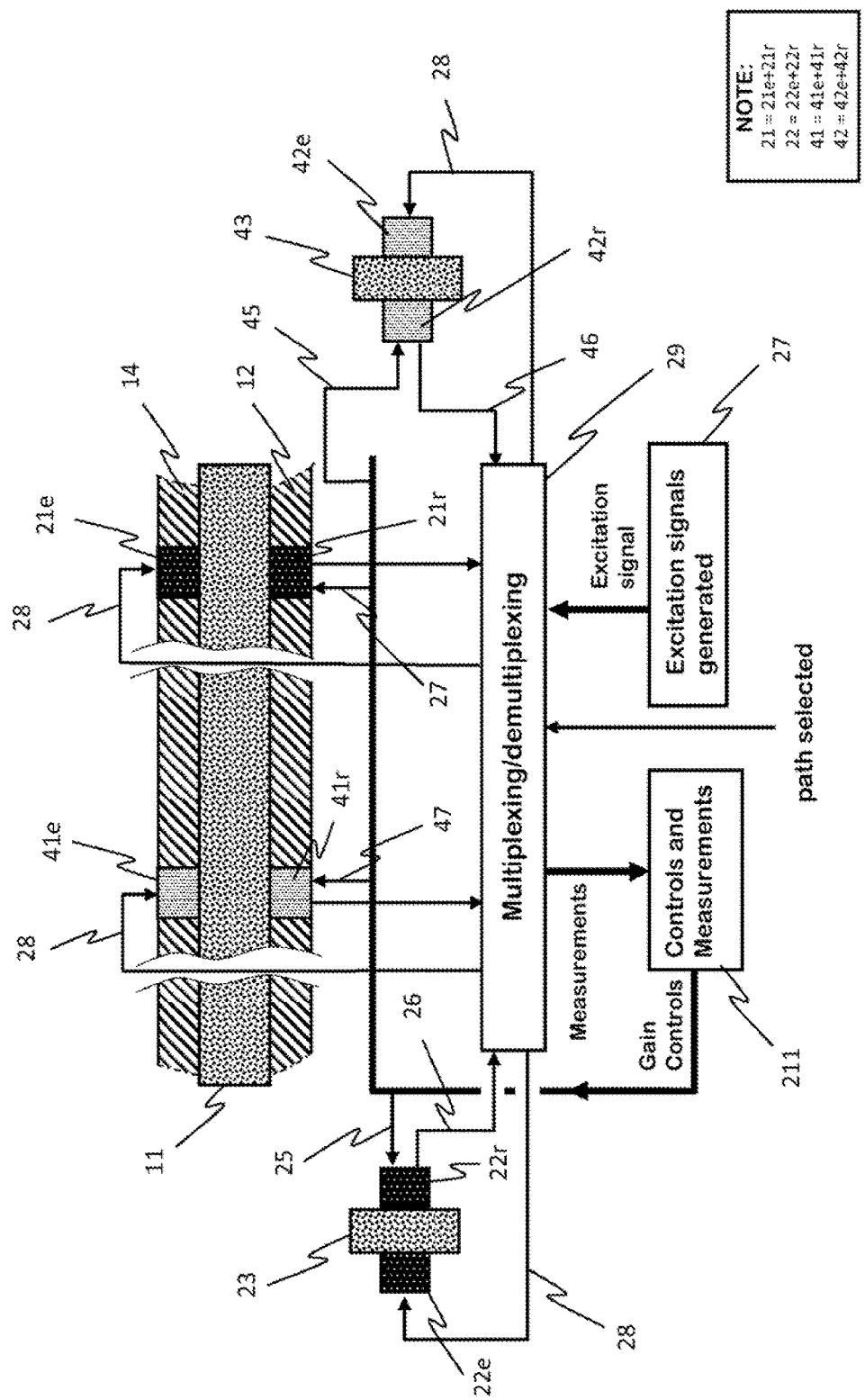
FIG. 4, a schematic representation of an embodiment of the automatic calibration method according to the invention in the context of the LRI method illustrated by FIG. 1.

Consequently, in operation, the calibration and measurement sensors alternately receive an excitation signal produced by a generator 29, this signal being alternately delivered to the various sensors, i.e. the measurement sensors 21, 41 or reference sensors 22, 42, via a multiplexing/demultiplexing circuit 44 controlled by a control unit, for example the test system computer (not shown in FIG. 4).

In a configuration like the one illustrated by FIG. 4, when it is excited, the transmitter 21e, 41e, 22e or 42e of each sensor transmits an ultrasonic wave and the receiver 21r, 41r, 22r or 42r receives the echo resulting from the propagation of the wave transmitted through the part 11 or the reference block 23 or 43.

The corresponding measurement signal is transmitted to the means for processing the measurements 211 via the multiplexing/demultiplexing circuit 44. Each sensor of the system also receives a gain control 25, 45, 27 or 47, delivered by the measurement means 211 via the multiplexing/demultiplexing circuit 44.

Such a structure, which incorporates the calibration device into the measurement system as a whole, makes it possible to alternately drive all of the sensors so that the measurements themselves are performed alternately for each of the measurement sensors 21 or 41.

Similarly, the calibration operations are performed by successively driving the reference sensor 22 and the reference sensor 42 and by implementing the calibration method according to the invention for each of these sensors. The values of the reception gain controls 25, 45 thus determined during the calibration phase for the reference sensors are then applied to the reception gain controls of the corresponding measurement sensors. Thus, the value of the gain control 27 applied to the measurement sensors 21 of the same type as the calibration sensor 22 is that of the gain control 25 determined for the sensor 22 after the execution of the calibration procedure. Likewise, the value of the gain control 47 applied to the measurement sensors 41 of the same type as the calibration sensor 42 is that of the gain control 45 determined for the sensor 42 after the execution of the calibration procedure.

It should be noted that, insofar as in the case illustrated by FIG. 2 the calibration device according to the invention is largely integrated into the overall test system responsible for driving the test sensors 21 and 41 and for processing the measurements collected by the measurement and control means 211, it is the central computer of the test system, not shown here, that implements the algorithm describing the method for calibrating each of the reference sensors 22 and 42.

To this end, in the calibration phase, it controls the excitation of one of the reference sensors 22 or 42, and controls the acquisition of the measurements of the reception signal delivered by this sensor by iteratively modifying the value of the gain applied to said reference sensor in order to determine the optimal gain value. The calibration phase is successively executed for the various reference sensors.

Next, in the measurement phase, it activates the application of the optimal reception gain value determined for each of the reference sensors 22 or 42 to each of the measurement sensors 21 or 41 of the same type as the reference sensor in question.

Thus, as is clear from the above description, thanks to the implementation of the automatic calibration means according to the invention, the measurements performed on a composite material part composite during its production, by means of ultrasonic sensors, can be substantially improved. In essence, thanks to the calibration operations performed during production, the amplitude of the analyzed signal can be maintained at an optimal value and the variations in the amplitude of the signal delivered by a sensor subsequent to a variation in the specific reception gain of this sensor can be eliminated, so that any variation in the amplitude of this signal may be directly attributed to a variation in the structure of the part being produced, and particularly to a variation in the viscoelastic state of the resin, the density of the fibers, or the possible presence of bubbles or porosities.

The invention claimed is:

1. A device for automatically calibrating an array of ultrasonic measurement sensors for monitoring a structure of a composite material part during its production, comprising:
   an array of ultrasonic reference sensors placed in proximity to the composite material part and in an environment same as the composite material part, each ultrasonic reference sensor being mounted on a calibration block and configured to be actuated to perform an amplitude measurement of a reference echo constituted by an ultrasonic wave transmitted by said each ultrasonic reference sensor that passed through the calibration block on which said each ultrasonic reference sensor is mounted, the array of ultrasonic reference sensors comprising at least one ultrasonic reference sensor for each type of the ultrasonic measurement sensors used to monitor the structure of the composite material part;
   a signal generator to actuate said each ultrasonic reference sensor at predetermined times during a production process of the composite material part; and
   a controller to measure an amplitude of the reference echo received by said each ultrasonic reference sensor, to determine a value of a gain control to be applied to said each ultrasonic reference sensor to maintain the amplitude of the reference echo at a predetermined set point value, and to apply a second gain control to each ultrasonic measurement sensor, a value of the second gain control is a function of the value of the gain control determined for one of the array of ultrasonic reference sensors being of the same type as said each ultrasonic measurement sensor.

2. The device according to claim 1, wherein the calibration blocks are made of silicon carbide or steel.

3. The device according to claim 1, wherein each ultrasonic reference sensor is mounted on a separate calibration block.

4. The device according to claim 1, wherein the calibration block is made of a material from which a variation of an attenuation of the ultrasonic waves, passing through the calibration block, as a function of temperature and pressure is known.

5. A device for automatically calibrating an array of ultrasonic measurement sensors for monitoring a structure of a composite material part during its production, comprising:
   an array of ultrasonic reference sensors placed in proximity to the composite material part and in an environment same as the composite material part, each ultrasonic reference sensor being mounted on a calibration block and configured to be actuated to perform an amplitude measurement of a reference echo constituted by an ultrasonic wave transmitted by said each ultrasonic reference sensor that passed through the calibration block on which said each ultrasonic reference sensor is mounted, the array of ultrasonic reference sensors comprising at least one ultrasonic reference sensor for each type of the ultrasonic measurement sensors used to monitor the structure of the composite material part;
   a signal generator to actuate said each ultrasonic reference sensor at predetermined times during a production process of the composite material part; and
   a controller to measure an amplitude of the reference echo received by said each ultrasonic reference sensor, to determine a value of a gain control to be applied to said each ultrasonic reference sensor to maintain the amplitude of the reference echo at a predetermined set point value, and to apply a second gain control to each ultrasonic measurement sensor, a value of the second gain control is substantially equal to the value of the gain control determined for one of the array of ultrasonic reference sensors being of the same type as said each ultrasonic measurement sensor.

6. The device according to claim 5, wherein the calibration block is made of a material from which a variation of an attenuation of the ultrasonic waves, passing through said calibration block, as a function of temperature and pressure is known.

7. The device according to claim 5, wherein the calibration blocks are made of silicon carbide or steel.

8. The device according to claim 5, wherein each ultrasonic reference sensor is mounted on a separate calibration block.

9. A method for automatically calibrating an array of ultrasonic measurement sensors for monitoring a structure of a composite material part during its production, comprising the steps of:

(a) applying an excitation signal to an reference sensor of an array of reference sensors to transmit an ultrasonic wave through a reference block on which said reference sensor is mounted and measuring an amplitude of a reference echo received by said reference sensor, the array of reference sensors being placed in proximity to the composite material in an environment same as the composite material part, and comprising at least one reference sensor for each type of the ultrasonic measurement sensors used to monitor the structure of the composite material part;

(b) determining a value of the gain control to be applied to said reference sensor to obtain a reference signal with an amplitude value substantially equal to a set point value;

(c) assigning the gain control determined for said reference sensor to the array of ultrasonic measurement sensors of a same type as said reference sensor;

(d) repeating the steps (a)-(c) for each reference sensor of the array of reference sensors at least once for each cycle of a process for producing the composite material part.

* * * * *